United States Patent
Melkent et al.

(10) Patent No.: US 10,973,651 B2
(45) Date of Patent: *Apr. 13, 2021

(54) INTERBODY SPINAL FUSION DEVICE

(71) Applicant: Warsaw Orthopedic, Inc., Warsaw, IN (US)

(72) Inventors: Anthony J. Melkent, Germantown, TN (US); Keith E. Miller, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/353,298

(22) Filed: Mar. 14, 2019

(65) Prior Publication Data

US 2019/0201213 A1 Jul. 4, 2019

Related U.S. Application Data

(63) Continuation of application No. 15/264,114, filed on Sep. 13, 2016, now Pat. No. 10,265,189.

(51) Int. Cl.
*A61F 2/44* (2006.01)

(52) U.S. Cl.
CPC .......... *A61F 2/4455* (2013.01); *A61F 2/4465* (2013.01)

(58) Field of Classification Search
CPC .......... A61F 2/44; A61F 2/4455; A61F 2/446; A61F 2/4465; A61F 2/447
See application file for complete search history.

(56) References Cited

U.S. PATENT DOCUMENTS 5,609,635 A * 3/1997 Michelson .............. A61F 2/442
623/17.16
5,702,449 A 12/1997 McKay
(Continued)

FOREIGN PATENT DOCUMENTS

CN 1901854 1/2007
WO 964014 12/1996
(Continued)

OTHER PUBLICATIONS

EP Extended Search Report dated Jan. 19, 2018 for EP17189531.1.
Office Action dated Dec. 1, 2020 in corresponding Chinese Application No. 201710817903.2.

*Primary Examiner* — Eric S Gibson (57) ABSTRACT

A spinal fusion implant includes a leading end, an opposite trailing end, an upper portion extending between the leading and trailing ends, a lower portion extending between the leading and trailing ends, and opposed first and second side portions extending between the leading and trailing ends. The upper portion includes at least two rails extending between the leading and trailing ends, the at least two rails including a first rail and a second rail spaced apart from one another, the first rail of the upper portion including a bone-contacting surface being at least partially smoothened. The lower portion includes at least two rails extending between the leading and trailing ends, the at least two rails including a first rail and a second rail spaced apart from one another, the first rail of the lower portion including a bone-contacting surface being at least partially smoothened.

20 Claims, 7 Drawing Sheets

(56) References Cited

U.S. PATENT DOCUMENTS

| | | | | |
|---|---|---|---|---|
| 6,059,829 | A * | 5/2000 | Schlapfer | A61F 2/4601 623/17.16 |
| 6,558,424 | B2 * | 5/2003 | Thalgott | A61F 2/4455 623/17.16 |
| 6,673,075 | B2 | 1/2004 | Santilli | |
| 6,923,810 | B1 | 8/2005 | Michelson | |
| 7,044,972 | B2 * | 5/2006 | Mathys, Jr. | A61F 2/4455 623/17.16 |
| D566,276 | S * | 4/2008 | Blain | D24/155 |
| 7,537,616 | B1 * | 5/2009 | Branch | A61F 2/446 623/17.16 |
| 7,914,554 | B2 | 3/2011 | Michelson | |
| 8,172,877 | B2 | 5/2012 | Winslow et al. | |
| 8,480,749 | B2 | 7/2013 | Ullrich, Jr. et al. | |
| 8,496,710 | B2 * | 7/2013 | Bagga | A61F 2/4465 623/17.16 |
| 8,562,684 | B2 * | 10/2013 | Ullrich, Jr. | A61F 2/4465 623/17.16 |
| 8,585,766 | B2 | 11/2013 | Ullrich, Jr. et al. | |
| 8,585,767 | B2 * | 11/2013 | Ullrich, Jr. | A61F 2/447 623/17.16 |
| 8,758,442 | B2 | 6/2014 | Ullrich, Jr. et al. | |
| 8,758,443 | B2 | 6/2014 | Ullrich, Jr. et al. | |
| 8,814,939 | B2 | 8/2014 | Ullrich, Jr. et al. | |
| 8,834,571 | B2 | 9/2014 | Bagga et al. | |
| 8,992,622 | B2 | 3/2015 | Ullrich, Jr. et al. | |
| 9,011,546 | B2 | 4/2015 | Ullrich, Jr. et al. | |
| 9,125,756 | B2 | 9/2015 | Ullrich, Jr. et al. | |
| 9,327,051 | B2 | 5/2016 | Ullrich, Jr. et al. | |
| 9,433,511 | B2 | 9/2016 | Bagga et al. | |
| 9,687,356 | B1 | 6/2017 | Spangler et al. | |
| 10,265,189 | B2 * | 4/2019 | Melkent | A61F 2/4455 |
| 2002/0161443 | A1 * | 10/2002 | Michelson | A61F 2/30749 623/17.11 |
| 2005/0131544 | A1 | 6/2005 | Kuras et al. | |
| 2006/0247770 | A1 * | 11/2006 | Peterman | A61F 2/4611 623/17.11 |
| 2006/0293748 | A1 * | 12/2006 | Alexander | A61F 2/447 623/17.11 |
| 2007/0260320 | A1 * | 11/2007 | Peterman | A61F 2/447 623/17.16 |
| 2007/0293949 | A1 * | 12/2007 | Salerni | A61F 2/4455 623/17.16 |
| 2008/0015702 | A1 | 1/2008 | Lakin et al. | |
| 2008/0195209 | A1 * | 8/2008 | Garcia | A61F 2/4455 623/17.16 |
| 2010/0204798 | A1 * | 8/2010 | Gerbec | A61F 2/4611 623/17.16 |
| 2011/0224796 | A1 * | 9/2011 | Weiland | B22F 3/1055 623/17.16 |
| 2012/0239152 | A1 * | 9/2012 | Ullrich, Jr. | A61F 2/4465 623/17.16 |
| 2012/0277876 | A1 * | 11/2012 | Ullrich, Jr. | A61F 2/447 623/17.16 |
| 2012/0283834 | A1 | 11/2012 | Gottlieb et al. | |
| 2012/0303127 | A1 * | 11/2012 | Ullrich, Jr. | A61F 2/4455 623/17.16 |
| 2012/0312779 | A1 | 12/2012 | Patterson et al. | |
| 2012/0316650 | A1 * | 12/2012 | Ullrich, Jr. | A61F 2/4465 623/17.16 |
| 2013/0096685 | A1 | 4/2013 | Ciupik et al. | |
| 2013/0116793 | A1 * | 5/2013 | Kloss | A61F 2/442 623/17.16 |
| 2013/0282122 | A1 | 10/2013 | Ullrich, Jr. et al. | |
| 2014/0031942 | A1 | 1/2014 | Ullrich, Jr. et al. | |
| 2014/0100657 | A1 * | 4/2014 | McCormack | A61B 17/1604 623/17.11 |
| 2014/0277511 | A1 | 9/2014 | Ullrich, Jr. et al. | |
| 2014/0288650 | A1 * | 9/2014 | Hunt | A61F 2/30907 623/16.11 |
| 2015/0351929 | A1 | 12/2015 | Ullrich, Jr. et al. | |
| 2016/0058574 | A1 | 3/2016 | Patterson et al. | |
| 2017/0156878 | A1 * | 6/2017 | Tsai | A61B 17/86 |
| 2018/0071113 | A1 * | 3/2018 | Melkent | A61F 2/4455 |
| 2018/0104063 | A1 * | 4/2018 | Asaad | A61F 2/447 |
| 2019/0201213 | A1 * | 7/2019 | Melkent | A61F 2/4455 |

FOREIGN PATENT DOCUMENTS

| | | |
|---|---|---|
| WO | 9723175 | 7/1997 |
| WO | 0185069 | 11/2001 |
| WO | 2007003437 | 1/2007 |
| WO | 2009154560 | 12/2009 |
| WO | 2013181234 | 12/2013 |
| WO | 2015187038 | 12/2015 |

* cited by examiner

INTERBODY SPINAL FUSION DEVICE

CROSS-REFERENCE TO RELATED APPLICATIONS

This application is a continuation of U.S. application Ser. No. 15/264,114, filed Sep. 13, 2016, all of which is incorporated by reference herein.

BACKGROUND OF THE INVENTION

Field of the Invention

The present invention relates to an interbody spinal fusion device for insertion into a disc space between adjacent vertebral bodies. More specifically, the present invention relates to an interbody spinal fusion device having an upper portion and a lower portion configured to facilitate ease of insertion into a disc space between adjacent vertebral bodies. More specifically, the present invention relates to an interbody spinal fusion device including rails provided on each of an upper portion and a lower portion of the implant, the rails extending above and below surfaces of the upper portion and the lower portion to contact adjacent vertebral bodies to facilitate ease of insertion of the implant into a disc space between the adjacent vertebral bodies.

Description of the Prior Art

Some of the degenerative conditions that affect the spine of a patient may be so severe as to require surgical intervention. Oftentimes, the degenerative conditions are such that a spinal implant is required to restore the height of a disc space between adjacent vertebral bodies. Such spinal implants are insertable into the disc space between the adjacent vertebral bodies of adjacent vertebrae of the patient. Oftentimes, such spinal implants are configured for push-in insertion into the disc space, and require fastening or holding features to maintain the positions thereof in the disc space. However, such fastening or holding features can serve in resisting push-in insertion of the spinal implants into the disc space. Therefore, there is a need for a spinal implant that includes fastening or holding features, and also includes features facilitating insertion into the disc space.

SUMMARY OF THE INVENTION

The present invention in one preferred embodiment contemplates a spinal fusion implant including a leading end, an opposite trailing end, an upper portion extending between the leading and trailing ends, and a lower portion extending between the leading and trailing ends, the upper portion including a first portion positioned adjacent the leading end, a second portion positioned adjacent the trailing end, and at least two rails extending between the first and second portions of the upper portion, the lower portion including a first portion positioned adjacent the leading end, a second portion positioned adjacent the trailing end, and at least two rails extending between the first and second portions of the lower portion, the at least two rails of the upper portion including a first rail including a bone-contacting surface being at least partially smoothened and a second rail including a bone-contacting surface, and the at least two rails of the lower portion including a first rail including a bone-contacting surface being at least partially smoothened and a second rail including a bone-contacting surface, where the first rail of the upper portion and the first rail of the lower portion facilitate insertion of the implant into a disc space between adjacent vertebrae, and the second rail of the upper portion and the second rail of the lower portion serve in holding the implant in position between the adjacent vertebrae.

The present invention in another preferred embodiment contemplates a spinal fusion implant including a leading end, an opposite trailing end, an upper portion extending between the leading and trailing ends, a lower portion extending between the leading and trailing ends, a first side portion extending between the leading and trailing ends, and a second side portion extending between the leading and trailing ends, the first and second side portion being opposite from one another, the upper portion including a first portion adjacent the leading end, a second portion adjacent the trailing end, and first, second, and third rails spaced apart from one another and extending between the first and second portions of the upper portion, the lower portion including a first portion adjacent the leading end, a second portion adjacent the trailing end, and first, second, and third rails spaced apart from one another and extending between the first and second portions of the lower portion, the first rail of the upper portion being positioned between the second and third rails of the upper portion, the first rail of the lower portion being positioned between the second and third rails of the lower portion, the second rails of the upper and lower portions being positioned adjacent the first side portion, and the third rails of the upper and lower portions being positioned adjacent the second side portion, where the first rails of the upper and lower portions include bone-contacting surfaces being at least partially smoothened, and where the second and third rails of the upper and lower portions include bone-contacting surfaces.

The present invention in yet another preferred embodiment contemplates a spinal fusion implant including a leading end, an opposite trailing end, an upper portion extending between the leading and trailing ends, a lower portion extending between the leading and trailing ends, and opposed first and second side portions extending between the leading and trailing ends, the upper portion including at least two rails extending between the leading and trailing ends, the at least two rails including a first rail and a second rail spaced apart from one another, the first rail of the upper portion including a bone-contacting surface being at least partially smoothened, the lower portion including at least two rails extending between the leading and trailing ends, the at least two rails including a first rail and a second rail spaced apart from one another, the first rail of the lower portion including a bone-contacting surface being at least partially smoothened.

These and other objects of the present invention will be apparent from review of the following specification and the accompanying drawings.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

An implant according to the present invention is generally indicated by the numeral 10 in FIGS. 1-8. The implant 10 is a spinal interbody fusion implant. As discussed below, the implant 10 is configured for insertion into a disc space between adjacent vertebrae, and is configured to allow bone growth therethrough between endplates of the adjacent vertebrae.

As depicted in FIGS. 1-8, the implant 10 includes a first end generally indicated by the numeral 12 and a second end generally indicated by the numeral 14. The first end 12 and the second end 14 are opposite from one another. Furthermore, the implant 10 includes a hollow cavity 16 positioned between the first end 12 and the second end 14. As discussed below, the hollow cavity 16 can be filled with bone growth promoting substances. Together with the configuration of the implant 10, the bone growth promoting substances can promote growth of bone through the implant 10 between the endplates of the adjacent vertebrae and onto the surfaces of the implant, particularly the roughened surfaces.

The first end 12 is the leading end of the implant 10, and the second end 14 is the trailing end of the implant 10. As depicted in FIGS. 1-4, the first end 12 is configured to facilitate insertion of the implant 10 into the disc space, and the second end 14 is configured to facilitate engagement of an insertion instrument (not shown) used to insert the implant 10 into the disc space. To that end, the first end 12 includes a nose portion 20 facilitating the insertion of the implant 10 into the disc space, and the second end 14 includes various tool engaging apertures/slots facilitating engagement with the insertion instrument. For example, the nose portion 20 has a rounded wedge shape configuration, and the configuration of the nose portion 20 affords introduction of the implant 10 into the disc space via slidable engagement with and separation of the adjacent vertebrae. Furthermore, the second end portion 14 can include a threaded aperture 22 and slots 26 facilitating engagement with the insertion instrument, and the engagement therebetween allows manipulation of the implant 10 using the insertion instrument.

Figure 1:
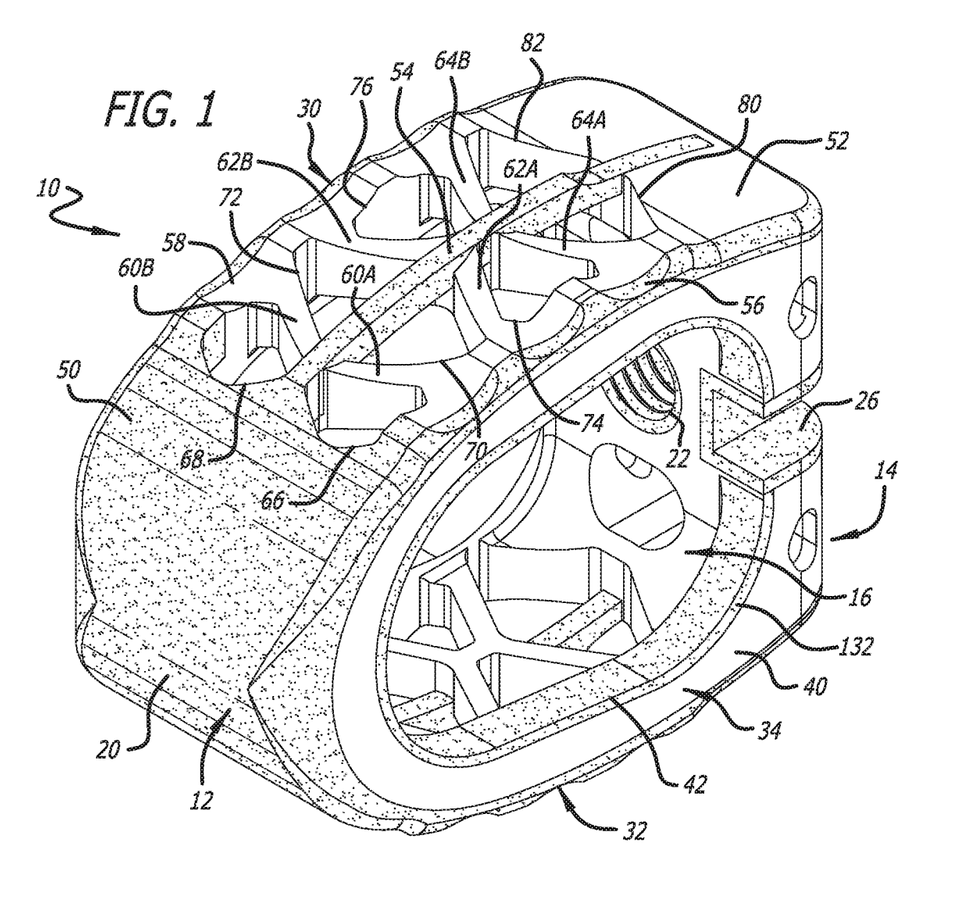
FIG. 1 is a top front perspective view of an interbody spinal fusion device according to the present invention.
Figure 2:
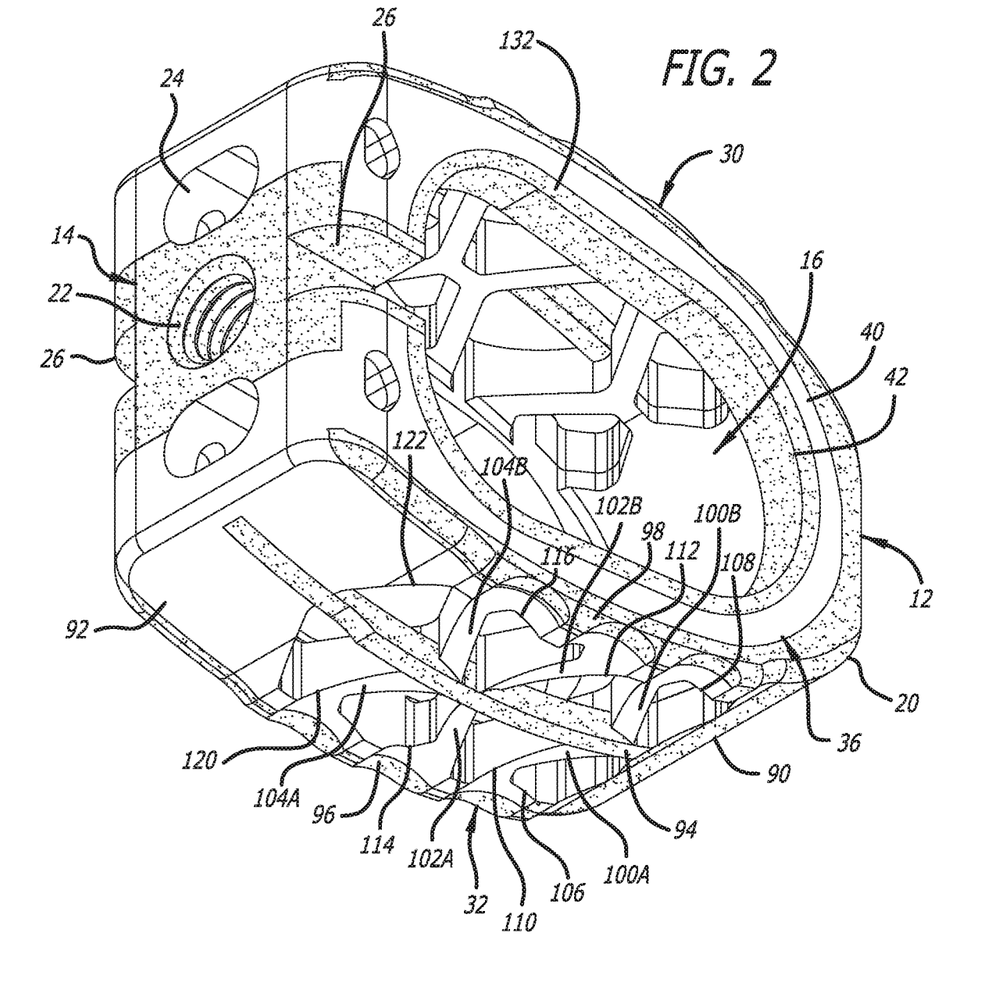
FIG. 2 is a bottom rear perspective view of the interbody spinal fusion device depicted in FIG. 1.
Figure 3:
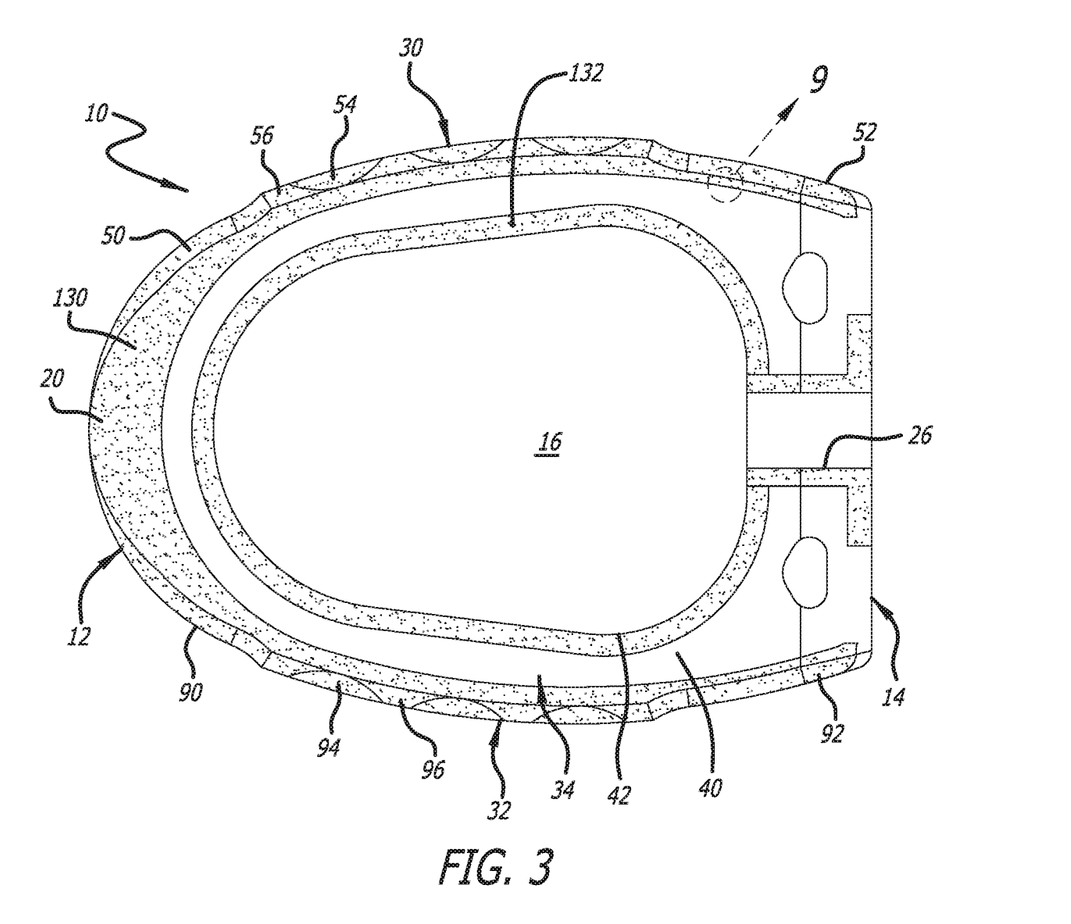
FIG. 3 is a right side elevational view of the interbody spinal fusion device of FIG. 1.
Figure 4:
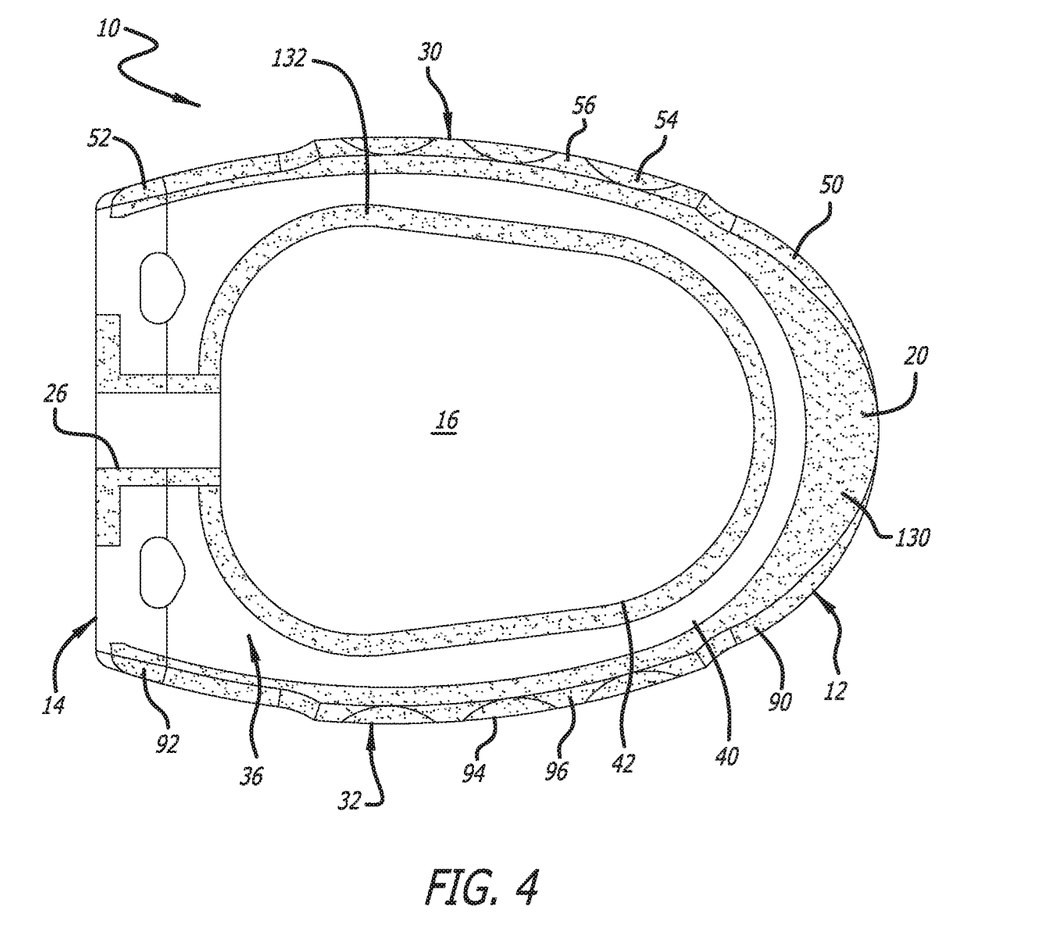
FIG. 4 is a left side elevational view of the interbody spinal fusion device of FIG. 1.
Figure 5:
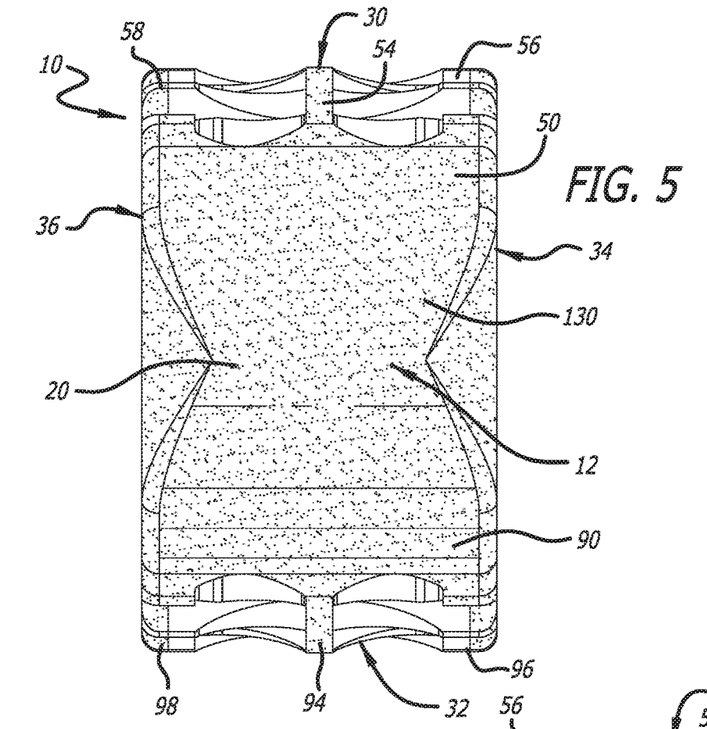
FIG. 5 is a front elevational view of the interbody spinal fusion device of FIG. 1.
Figure 6:
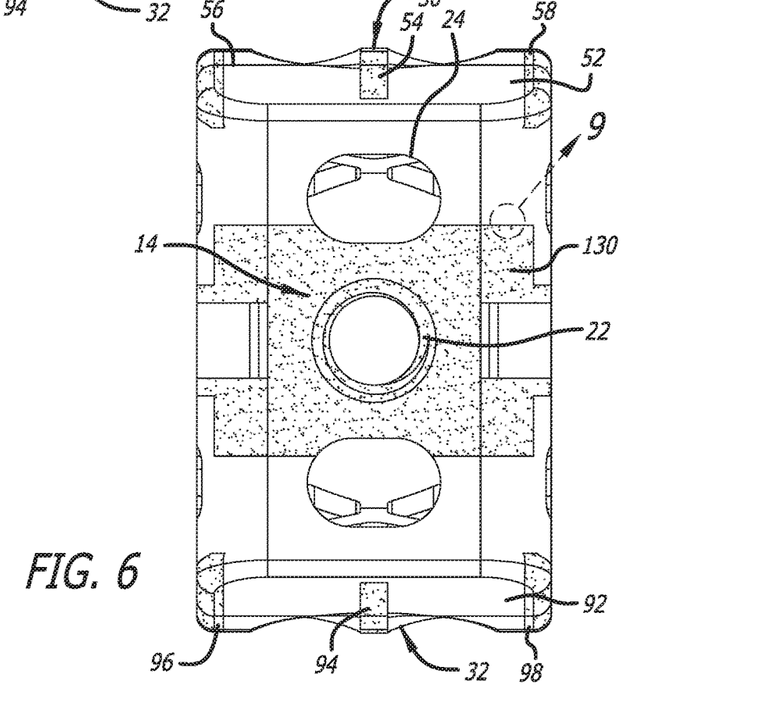
FIG. 6 is a rear elevational view of the interbody spinal fusion device of FIG. 1.
Figure 7:
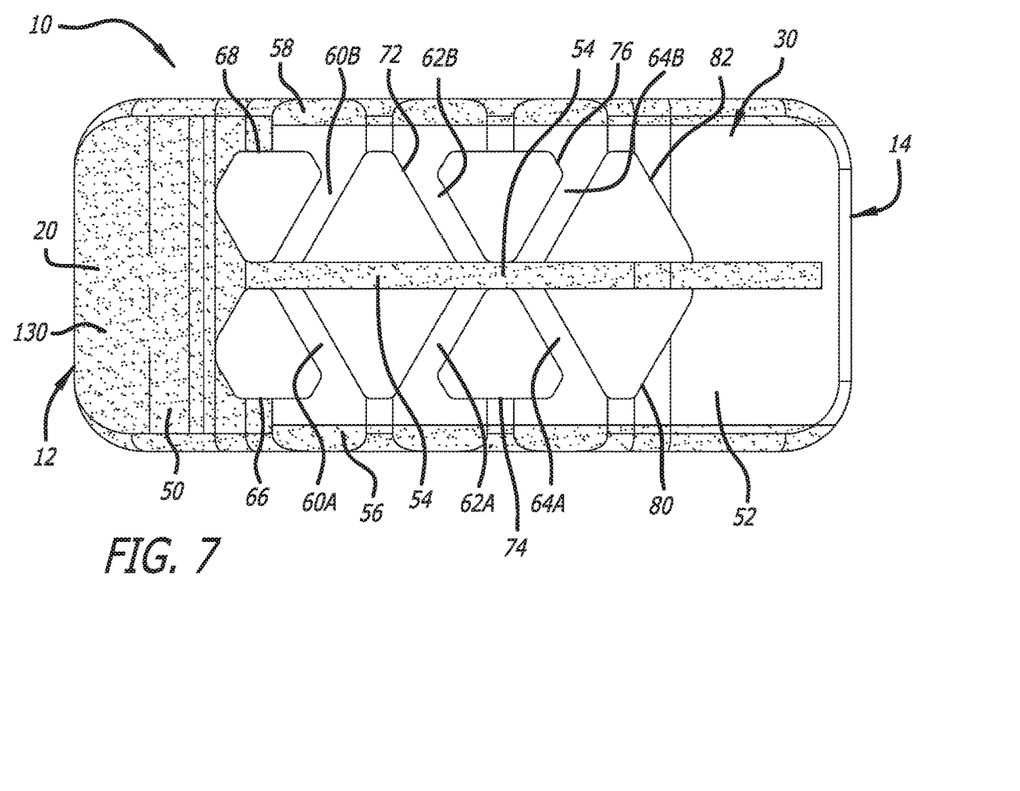
FIG. 7 is top plan view of the interbody spinal fusion device of FIG. 1.
Figure 8:
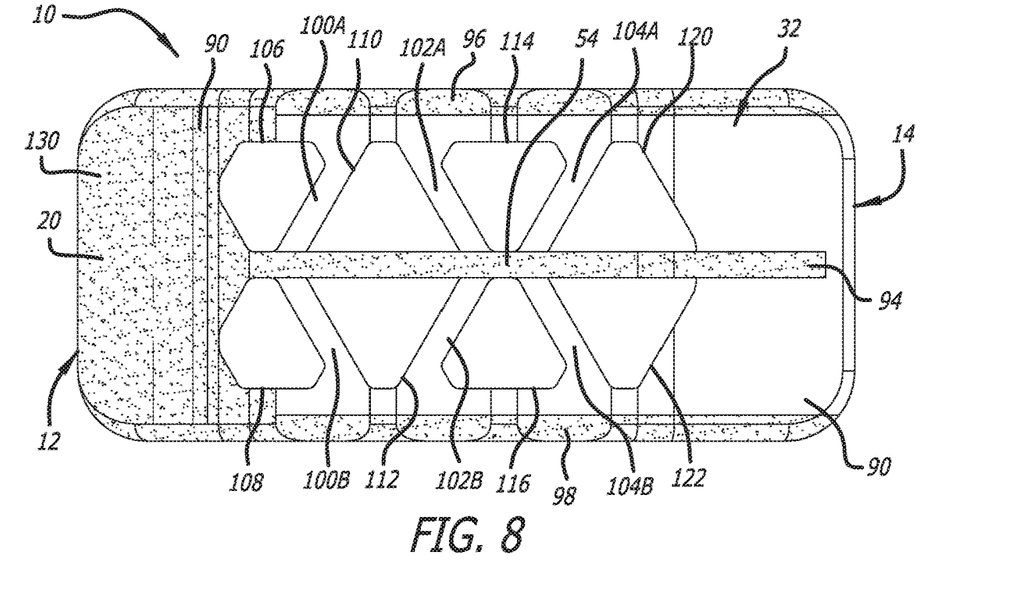
FIG. 8 is bottom plan view of the interbody spinal fusion device of FIG. 1.

As depicted in FIGS. 1 and 2, the implant includes an upper portion 30, a lower portion 32, a first side portion 34, and a second side portion 36. The first side portion 34 and the second side portion 36 each include portions extending adjacent the upper portion 30 and the lower portion 32 between the first and second ends 12 and 14. Furthermore, the first side portion 34 and the second side portion 36 each include a horseshoe-shaped surface 40 and an aperture 42 communicating with the hollow cavity 16. The hollow cavity 16 and the apertures 42 define a passage through the implant 10 between the first side portion 34 and the second side portion 36.

The upper portion 30 and the lower portion 32 each extend between the first and second ends 12 and 14. The upper portion 30 includes a forward portion 50 adjacent the first end 12, and a rearward portion 52 adjacent the second end 14. The forward portion 50 and the rearward portion 52 each include surfaces for engaging the endplate of the upper of the adjacent vertebrae. The upper portion 30 also includes first, second, and third rails 54, 56, and 58.

The first, second, third rails 54, 56, and 58 extend between the forward portion 50 and the rearward portion 52, and serve in joining the forward portion 50 and the rearward portion 52 together. The first, second, and third rails 54, 56, and 58 are also for engaging the endplate of the upper of the adjacent vertebrae. The first rail 54 is positioned between the second rail 56 and the third rail 58, the second rail 56 is positioned adjacent the first side portion 34, and the third rail 58 is positioned adjacent the second side portion 36. Various cross members 60A, 62A, and 64A extend between the first rail 54 and the second rail 56 to join these rails together, and various cross members 60B, 62B, and 64B extend between the first rail 54 and the third rail 58 to join these rails together.

Various apertures 66, 68, 70, 72, 74, 76, 80, and 82 are formed in the upper portion 30, and these apertures are bordered by at least two of the forward portion 50, the rearward portion 52, the first rail 54, the second rail 56, the third rail 58, and the cross members 60A, 60B, 62A, 62B, 64A, and 64B. The apertures 66, 68, 70, 72, 74, 76, 80, and 82 extend through the upper portion 30, and communicate with the hollow cavity 16. The apertures 66, 68, 70, 72, 74, 76, 80, and 82 facilitate growth of bone from the upper of the adjacent vertebrae therethrough and into the hollow cavity 16.

The first aperture 66 is at least bordered by the forward portion 50, the first rail 54, the second rail 56, and the cross member 60A. The second aperture 68 is at least bordered by the forward portion 50, the first rail 54, the third rail 58, and the cross member 60B. The third aperture 70 is at least bordered by the first rail 54, the cross member 60A, and the cross member 62A. The fourth aperture 72 is at least bordered by the first rail 54, the cross member 60B, and the cross member 62B. The fifth aperture 74 is at least bordered by the second rail 56, the cross member 62A, and the cross member 64A. The sixth aperture 76 is at least bordered by the third rail 58, the cross member 62B, and the cross member 64B. The seventh aperture 80 is at least bordered by the rearward portion 52, the first rail 54, and the cross member 64A. The eighth aperture 82 is at least bordered by the rearward portion 52, the first rail 54, and the cross member 64B.

As depicted in FIG. 1, the first rail 54 has a smoothened upper surface. Furthermore, although both are depicted as being at least partially serrated in FIG. 1, the second rail 56 can have a smoothened and/or a serrated upper surface, and the third rail 58 can have a smoothened and/or a serrated upper surface. When provided therewith, the smoothened upper surface of the first rail 54 serves in aiding the insertion of the implant 10 into the disc space between the adjacent vertebrae. When the upper surfaces of the second and third rails 56 and 58 are at least partially smoothened, the second and third rails 56 and 58 can serve in aiding the insertion of the implant 10 into the disc space. Moreover, when the upper surfaces of the second and third rails 56 and 58 are at least partially serrated, the second and third rails 56 and 58 can serve in resisting movement of the implant 10 after positioning thereof in the disc space.

The lower portion 32 includes a forward portion 90 adjacent the first end 12, and a rearward portion 92 adjacent the second end 14. The forward portion 90 and the rearward portion 92 each include surfaces for engaging the endplate of the lower of the adjacent vertebrae. The lower portion 32 also includes first, second, and third rails 94, 96, and 98.

The first, second, and third rails 94, 96, and 98 extend between the forward portion 90 and the rearward portion 92, and serve in joining the forward portion 90 and the rearward portion 92 together. The first, second, and third rails 94, 96, and 98 are also for engaging the endplate of the lower of the adjacent vertebrae. The first rail 94 is positioned between the second rail 96 and the third rail 98, the second rail 96 is positioned adjacent first side portion 34, and the third rail 98 is positioned adjacent the second side portion 36. Various cross members 100A, 102A, and 104A extend between the first rail 94 and the second rail 96 to join these rails together, and various cross members 100B, 102B, and 104B extend between the first rail 94 and the third rail 96 to join these rails together.

Various apertures 106, 108, 110, 112, 114, 116, 120, 122 are formed in the lower portion 32, and these apertures are bordered by at least two of the forward portion 90, the rearward portion 92, the first rail 94, the second rail 96, the third rail 98, and the cross members 100A, 100B, 102A, 102B, 104A, and 104B. The apertures 106, 108, 110, 112, 114, 116, 120, 122 are formed and extend through the lower portion 32, and communicate with the hollow cavity 16. The apertures 106, 108, 110, 112, 114, 116, 120, 122 facilitate growth of bone from the lower of the adjacent vertebrae therethrough and into the hollow cavity 16.

The first aperture 106 is at least bordered by the forward portion 90, the first rail 94, the second rail 96, and the cross member 100A. The second aperture 108 is at least bordered by the forward portion 90, the second rail 96, and the cross member 100B. The third aperture 110 is at least bordered by the first rail 94, the cross member 100A, and the cross member 102A. The fourth aperture 112 is at least border by the first rail 94, the cross member 100B, and the cross member 102B. The fifth aperture 114 is at least bordered by the second rail 96, the cross member 102A, and the cross member 104A. The sixth aperture 116 is at least bordered by the third rail 98, the cross member 102B, and the cross member 104B. The seventh aperture 120 is at least bordered by the rearward portion 92, the first rail 54, and the cross member 104A. The eighth aperture 122 is at least bordered by the rearward portion 92, the first rail 94, and the cross member 104B.

As depicted in FIG. 2, the first rail 94 has a smoothened lower surface. Furthermore, although both are depicted as being at least partially serrated in FIG. 2, the second rail 96 can have a smoothened and/or a serrated lower surface, and the third rail 98 can have a smoothened and/or a serrated lower surface. When provided therewith, the smoothened lower surface of the first rail 94 serves in aiding the insertion of the implant 10 into the disc space between the adjacent vertebrae. When the lower surfaces of the second and third rails 96 and 98 are at least partially smoothened, the second and third rails 96 and 98 can serve in aiding the insertion of the implant 10 into the disc space. Moreover, when the lower surfaces of the second and third rails 96 and 98 are at least partially serrated, the second and third rails 96 and 98 can serve in resisting movement of the implant 10 after positioning thereof in the disc space.

During insertion of the implant 10 into the disc space between adjacent vertebrae, the nose portion 20 of the first end 12, the forward portion 50 of the upper portion 30, and the forward portion 90 of the lower portion 32 first engage the adjacent vertebrae. In doing so, the nose portion 20 engages the upper and lower vertebrae, the forward portion 50 engages the upper vertebra, and the forward portion 90 engages the lower vertebra. Because of the rounded wedge shape of the nose portion 20, and because the forward portions 50 and 52 are angled with respect to one another, the adjacent vertebrae are wedged apart from one another as the nose portion 20, the forward portion 50, and the forward portion 90 are pushed into engagement thereto.

As the implant is pushed further into the disc space, the first rail 54 of the upper portion 30 and the first rail 94 of the lower portion 32 engage the upper and lower vertebrae, respectively. Portions of the upper surface of the first rail 54 and portions of the lower surface of the first rails 94 are raised above and below, respectively, the remainder of the upper portion 30 and the lower portion 32. Thus, given that the upper and lower surfaces of the first rails 54 and 94 are smoothened, the implant 10 slides on the first rails 54 and 94 during insertion of the implant 10 into the disc space. In other words, the upper surface of the first rail 54 and the lower surface of the first rail 94 provide mediums on which the implant 10 can slide during entry thereof into the disc space. When the upper surfaces of the second and third rails 56 and 58 and the lower surfaces of the second and third rails 96 and 98 are at least partially smoothened, these surfaces can also serve in aiding the insertion of the implant 10 into the disc space.

Once positioned in the disc space, the upper surfaces, if serrated, of the second and third rails 56 and 58, and the lower surfaces, if serrated, of the second and third rails 96 and 98 serve in resisting movement of the implant 10. If serrated, much of the upper surfaces of the second and third rails 56 and 58 would be positioned below the upper surface of the first rail 54, and, if serrated, much of the lower surfaces of the second and third rails 56 and 58 are positioned above the lower surface of the first rail 94. That is, when looking at FIGS. 3 and 4 (i.e., the right and left side elevational views of the implant 10), the first rail 54 has a larger profile than the second and third rails 56 and 58 due to the serrations, and the first rail 94 has a larger profile than the second and third rails 96 and 98 due to the serrations. The first rails 54 and 94 can also be configured to have larger or smaller profiles than the second rails 56 and 96 and/or the third rails 58 and 98.

The endplates of the upper and lower vertebrae are generally concave between the anterior and posterior portions thereof and between the lateral sides thereof. Thus, when the implant 10 is inserted anteriorly or posteriorly and positioned between the endplates, the first rail 54 can be contacted to a more upper portion of the upper endplate than the portions of the upper endplate contacted by the second and third rails 56 and 58, and the first rail 94 can be contacted to a more lower portion of the lower endplate than the portions of the lower endplate contacted by the second and third rails 96 and 98. As discussed above, when provided with serrations, contact of the serrations of the second rails 56 and 96 and the third rails 58 and 98 serve in resisting movement of the implant 10 after implantation into the disc space.

Figure 9:
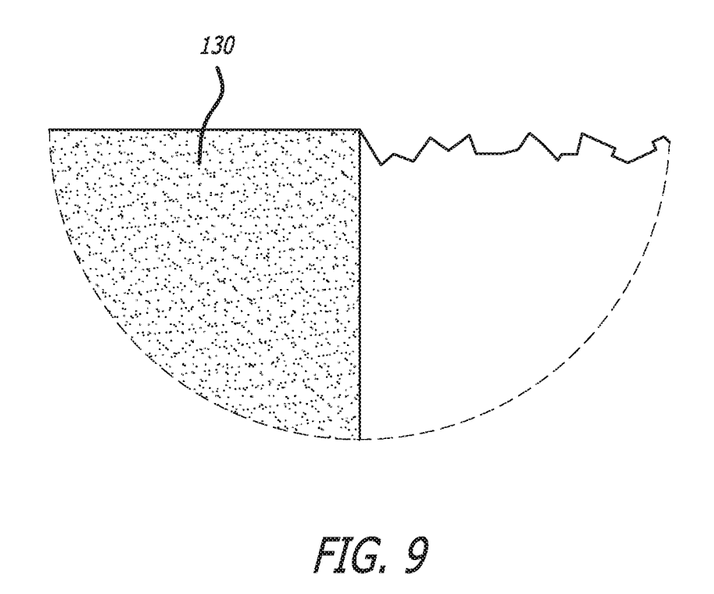
FIG. 9 is a partial side view of the surface of the interbody spinal fusion device of FIG. 1 showing examples of different surface textures.

The implant 10 can be manufactured using Additive Manufacturing Methods. Using Additive Manufacturing Methods, the various surfaces of the implant 10 can be provided with different textures, and these textures can be used to afford ease of insertion of the implant 10 into the disc space, or used to facilitate bone growth into the implant 10. An example of Additive Manufacturing Methods is Direct Metal Laser Sintering. For example, portions of the nose portion 20, the first, second, and third rails 54, 56, and 58, and the first, second, third, rails 94, 96, and 98 can be manufactured to include smoothened surfaces as depicted in FIG. 9, and the remainder of the implant 10 can be manufactured to include roughened surfaces as depicted in FIG. 9. The reference to smoothened and roughened surfaces denotes a relative difference between the textures of these surfaces. As such, the smoothened surfaces can be somewhat rough, but be considerably smoother than the roughened surfaces The smoothened surfaces can be provided to facilitate insertion of the implant 10 into the disc space, and the roughened surfaces can be provided to facilitate bone growth onto the implant 10. Thus, the various surfaces afforded by the use of Additive Manufacturing Methods facilitates (via smoothened surfaces) entry of the implant 10 into the disc space, and facilitates (via roughened surfaces) integration of the implant 10 into the upper and lower vertebrae. Additionally, the various surfaces of the implant 10 can be smoothened using a polishing process.

The location of the smoothened surfaces of the implant 10 are generally indicated by the numeral 130 and are represented by stippling in FIGS. 1-8. The remainder of the surfaces of the implant 10 can be roughened. For example, the cross members 60A, 60B, 62A, 62B, 64A, and 64B and the cross members 100A, 1006, 102A, 102B, 104A, and 104B, as well as rearward portions 52 and 92, can have roughened upper surfaces and roughened lower surfaces, respectively, that serve in resisting movement of the implant 10 after positioning thereof in the disc space. Settling of the implant 10 into the bone of the adjacent vertebrae causes increased contact with these roughened surfaces to increase resistance of the implant 10 to movement.

Additionally, as depicted in FIGS. 1-4, smoothened surfaces 132 can be provided on the surfaces 40 around the edges of apertures 42 and on the interior surfaces of the apertures 42. The smoothened surfaces 132 can provide smoothened edges at the transition of the surfaces 40 into the apertures 42.

It is also noted that the edges of the implant 10 can be rounded to minimize any potential harm to sensitive tissues during implantation of the implant 10. For example, in addition to the nose portion 20, the transitions between the upper portion 30 and the first and second side portions 34 and 36, and the transitions between the lower portion 32 and the first and second side portions 34 and 36 can also be rounded.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A spinal fusion implant comprising:
   a leading end, an opposite trailing end, a mid-longitudinal axis extending through the leading end and the trailing end, an upper portion extending between the leading and trailing ends, and a lower portion extending between the leading and trailing ends,
   the upper portion including a first portion positioned adjacent the leading end, a second portion positioned adjacent the trailing end, and at least two rails extending between the first and second portions of the upper portion,
   the lower portion including a first portion positioned adjacent the leading end, a second portion positioned adjacent the trailing end, and at least two rails extending between the first and second portions of the lower portion,
   the at least two rails of the upper portion including a first rail including a bone-contacting surface being smoothened and extending in a continuous convex curve from adjacent the first portion to adjacent the second portion of the upper portion, and a second rail including a bone-contacting surface, and
   the at least two rails of the lower portion including a first rail including a bone-contacting surface being smoothened and extending in a continuous convex curve from adjacent the first portion to adjacent the second portion of the lower portion, and a second rail including a bone-contacting surface.

2. The implant of claim 1, further comprising a first side portion and a second side portion opposite from one another, the first side portion extending between the leading end and the trailing end, and between the upper portion and the lower portion, and the second side portion extending between the leading end and the trailing end, and between the upper portion and the lower portion.

3. The implant of claim 2, further comprising a hollow cavity between the upper portion and the lower portion for receiving bone-growth promoting substances.

4. The implant of claim 3, further comprising a first aperture in the first side portion and a second aperture in the second side portion, the first and second apertures providing access to the hollow cavity, the first side portion including a smoothened surface adjacent edges forming at least a portion of the perimeter of the first aperture, the second side portion including a smoothened surface adjacent edges forming at least a portion of the perimeter of the second aperture, and the first and second side portions including portions having roughened surfaces.

5. The implant of claim 1, further comprising at least a first cross member and a second cross member extending in an area between the first and second rails of the upper portion, and at least a first cross member and a second cross member extending in an area between the first and second rails of the lower portion, wherein the first cross member and the second cross member of the upper portion define at least a portion of a first aperture through the upper portion, and the first cross member and the second cross member of the lower portion define at least a portion of a first aperture through the lower portion.

6. The implant of claim 5, wherein each of the first aperture through the upper portion and the first aperture through the lower portion communicates with a hollow cavity in the implant, wherein bone fusion can occur through the first aperture in the upper portion, the first aperture in the lower portion, and the hollow cavity.

7. The implant of claim 1, wherein portions of the leading end of the implant, the bone-contacting surface of the first rail of the upper portion, and the bone-contacting surface of the first rail of the lower portion being smoothened using one of an additive metal manufacturing process and a polishing process.

8. The implant of claim 1, wherein portions of the upper portion, the lower portion, the first side portion, and the second side portion have roughened surfaces affording bone ingrowth.

9. A spinal fusion implant comprising:
a leading end, an opposite trailing end, a mid-longitudinal axis extending through the leading end and the trailing end, an upper portion extending between the leading and trailing ends, a lower portion extending between the leading and trailing ends, a first side portion extending between the leading and trailing ends, and a second side portion extending between the leading and trailing ends, the first and second side portion being opposite from one another,
the upper portion including a first portion adjacent the leading end, a second portion adjacent the trailing end, and a first rail and a second rail spaced apart from one another and extending between the first and second portions of the upper portion,
the lower portion including a first portion adjacent the leading end, a second portion adjacent the trailing end, and a first rail and a second rail spaced apart from one another and extending between the first and second portions of the lower portion, and
wherein at least one of the first rails and the second rails of each of the upper and lower portions include bone-contacting surfaces being smoothened and extending in continuous convex curves from adjacent the first portion to adjacent the second portion.

10. The implant of claim 9, further comprising a hollow cavity between the upper portion and the lower portion for receiving bone-growth promoting substances.

11. The implant of claim 10, further comprising a first aperture in the first side portion and a second aperture in the second side portion, the first and second apertures providing access to the hollow cavity, the first side portion including a smoothened surface adjacent edges forming at least a portion of the perimeter of the first aperture, the second side portion including a smoothened surface adjacent edges forming at least a portion of the perimeter of the second aperture, and the first and second side portions including portions having roughened surfaces.

12. The implant of claim 11, further comprising at least a first cross member and a second cross member extending in an area between the first rail and the second rail of the upper portion, wherein the first cross member and the second cross member of the upper portion define at least a portion of a first aperture through the upper portion, the first aperture communicating with the hollow cavity.

13. The implant of claim 11, further comprising at least a first cross member and a second cross member extending in an area between the first rail and the second rail of the lower portion, wherein the first cross member and the second cross member of the lower portion define at least a portion of a first aperture through the lower portion, the first aperture communicating with the hollow cavity.

14. The implant of claim 9, wherein portions of the leading end of the implant, and the bone-contacting surfaces of the first rails of the upper and lower portions are smoothened using one of an additive metal manufacturing process and a polishing process.

15. The implant of claim 9, wherein portions of the upper portion and portions of the lower portion have roughened surfaces affording bone ingrowth.

16. A spinal fusion implant comprising:
a leading end, an opposite trailing end, a mid-longitudinal axis extending through the leading end and the trailing end, an upper portion extending between the leading and trailing ends, a lower portion extending between the leading and trailing ends,
the upper portion including at least two rails extending between the leading and trailing ends, the at least two rails including a first rail and a second rail spaced apart from one another, the first rail of the upper portion including a bone-contacting surface being smoothened and extending in a continuous convex curve from adjacent the leading end to adjacent the trailing end, and
the lower portion including at least two rails extending between the leading and trailing ends, the at least two rails including a first rail and a second rail spaced apart from one another, the first rail of the lower portion including a bone-contacting surface being smoothened and extending in a continuous convex curve from adjacent the leading end to adjacent the trailing end.

17. The implant of claim 16, further comprising a hollow cavity between the upper portion and the lower portion for receiving bone-growth promoting substances.

18. The implant of claim 17, further comprising a first side portion extending between the upper portion and the lower portion, a second side portion extending between the upper portion and the lower portion, a first aperture in the first side portion, and a second aperture in the second side portion, the first and second apertures providing access to the hollow cavity, the first side portion including a smoothened surface adjacent edges forming at least a portion of the perimeter of the first aperture, the second side portion including a smoothened surface adjacent edges forming at least a portion of the perimeter of the second aperture, and the first and second side portions including portions having roughened surfaces.

19. The implant of claim 18, further comprising at least a first cross member and a second cross member extending in an area between the first rail and the second rail of the upper portion, wherein the first cross member and the second cross member of the upper portion define at least a portion of a first aperture through the upper portion, the first aperture communicating with the hollow cavity.

20. The implant of claim 19, further comprising at least a first cross member and a second cross member extending in an area between the first rail and the second rail of the lower portion, wherein the first cross member and the second cross member of the lower portion define at least a portion of a first aperture through the lower portion, the first aperture communicating with the hollow cavity.

* * * * *